US011446513B2

(12) United States Patent
Shanks (10) Patent No.: US 11,446,513 B2
(45) Date of Patent: Sep. 20, 2022

(54) METHODS OF TREATING AUTISM USING LIGHT THERAPY

(71) Applicant: Erchonia Corporation, Melbourne, FL (US)

(72) Inventor: Steven C Shanks, Melbourne, FL (US)

(73) Assignee: Erchonia Corporation, LLC, Melbourne, FL (US)

( * ) Notice: Subject to any disclaimer, the term of this patent is extended or adjusted under 35 U.S.C. 154(b) by 0 days.

(21) Appl. No.: 15/848,514

(22) Filed: Dec. 20, 2017

(65) Prior Publication Data

US 2018/0169436 A1   Jun. 21, 2018

Related U.S. Application Data

(63) Continuation-in-part of application No. 15/604,363, filed on May 24, 2017, now abandoned.

(60) Provisional application No. 62/435,326, filed on Dec. 16, 2016.

(51) Int. Cl.
| | |
|---|---|
| *A61N 5/06* | (2006.01) |
| *A61N 1/05* | (2006.01) |
| *A61N 1/36* | (2006.01) |
| *A61N 5/067* | (2006.01) |

(52) U.S. Cl.
CPC ......... *A61N 5/0622* (2013.01); *A61N 5/0618* (2013.01); *A61N 1/0536* (2013.01); *A61N 1/36025* (2013.01); *A61N 5/067* (2021.08); *A61N 2005/0643* (2013.01); *A61N 2005/0662* (2013.01)

(58) Field of Classification Search
CPC .. A61N 5/0622; A61N 5/0618; A61N 1/0536; A61N 1/36025; A61N 2005/067; A61N 2005/0643; A61N 2005/0662
See application file for complete search history.

(56) References Cited

U.S. PATENT DOCUMENTS

| | | | |
|---|---|---|---|
| 6,013,096 | A | 1/2000 | Tucek |
| 6,605,079 | B2 | 8/2003 | Shanks |
| 6,746,473 | B2 | 6/2004 | Shanks |
| 7,118,588 | B2 | 10/2006 | Tucek |

(Continued)

OTHER PUBLICATIONS

Applicant's Response to USPTO Office Action dated Dec. 13, 2017 for U.S. Appl. No. 15/604,363, submitted Feb. 19, 2018.

(Continued)

*Primary Examiner* — Gary Jackson
*Assistant Examiner* — Jessandra F Hough
(74) *Attorney, Agent, or Firm* — Etherton Law Group, LLC (57) ABSTRACT

A method for treating autism. Light energy is applied externally to a patient's scalp on the skull near the frontal lobes. Optionally the light is also applied to the temporal lobes and the base of the brain. The treatment can be enhanced by activating the cranial nerves while the light is applied. In a preferred embodiment the applied light is in the red range and more preferably about of 635 nm±10 nm. In a preferred embodiment, the applied light energy is applied with a pulse frequency or frequencies of 8 Hz, 53 Hz, 73 Hz and 101 Hz. The light can be emitted from the same light emitter or from multiple emitters. Preferably the light is laser light and is emitted as a line from a hand-held laser device, and the line is waved manually across a person's skull in the desired area in a continuous, sweeping manner.

16 Claims, 6 Drawing Sheets

(56) References Cited

U.S. PATENT DOCUMENTS

| | | | |
|---|---|---|---|
| 7,922,751 B2 | 4/2011 | Shanks | |
| 7,947,067 B2 | 5/2011 | Tucek | |
| 8,366,756 B2 | 2/2013 | Tucek | |
| 8,409,264 B2 | 4/2013 | Shanks | |
| 8,439,959 B2 | 5/2013 | Tucek | |
| 8,813,756 B1 | 8/2014 | Shanks | |
| 8,814,924 B2 | 8/2014 | Shanks | |
| 8,932,338 B2 | 1/2015 | Lim | |
| 9,149,650 B2 | 10/2015 | Shanks | |
| 9,730,649 B1* | 8/2017 | Jepsen | A61B 5/745 |
| 10,987,521 B1 | 4/2021 | Chicchi | |
| 2003/0109906 A1* | 6/2003 | Streeter | A61N 5/0613 607/88 |
| 2007/0179571 A1* | 8/2007 | De Taboada | A61N 5/0613 607/88 |
| 2009/0254154 A1* | 10/2009 | De Taboada | A61N 5/0613 607/88 |
| 2012/0046716 A1* | 2/2012 | Dougal | A61N 5/0613 607/91 |
| 2012/0089206 A1* | 4/2012 | Wu | A61N 5/0618 607/89 |
| 2013/0138182 A1* | 5/2013 | Nissila | A61N 5/0618 607/88 |
| 2013/0165846 A1* | 6/2013 | Peyman | A61N 5/062 604/20 |
| 2018/0015301 A1* | 1/2018 | Lim | A61N 5/0603 |

OTHER PUBLICATIONS

Applicant's Response to USPTO Office Action dated May 18, 2018 for U.S. Appl. No. 15/604,363, submitted Aug. 20, 2018.
Applicant's Request for Continued Examination and Response to USPTO Advisory Action dated Sep. 18, 2018 for U.S. Appl. No. 15/604,363, submitted Oct. 25, 2018.
Applicant's Response to USPTO Office Action dated Nov. 19, 2018 for U.S. Appl. No. 15/604,363, submitted Jan. 23, 2019.
Applicant's Response to USPTO Office Action dated Dec. 13, 2017 for U.S. Appl. No. 15/696,083, submitted Feb. 19, 2018.
Applicant's Request for Continued Examination and Response to USPTO Office Action dated May 18, 2018 for U.S. Appl. No. 15/604,363, submitted Nov. 14, 2018.

* cited by examiner

| Cranial Nerve | Fibers | Structures Innervated | Functions | Brainstem Nucleus |
|---|---|---|---|---|
| I Olfactory | Sensory | Olfactory epithelium (via olfactory bulb) | Olfaction | - |
| II Optic | Sensory | Retina | Vision | - |
| III Oculomotor | Motor | Superior/middle/inferior rectus, inferior oblique, levator palpebrae | Movement of eyeball | Oculomotor nucleus |
| | Parasympathetic | Pupillary constrictor, ciliary muscle of eyeball. Both via the ciliary ganglion | Pupillary constriction and accommodation | Oculomotor nucleus |
| IV Trochlear | Motor | Superior oblique | Movement of eyeball | Trochlear nucleus |
| V Trigeminal | Sensory | Face, scalp, cornea, nasal, and oral cavities, cranial dura mater | General sensation | Trigeminal sensory nucleus |
| | Motor | Muscles of mastication | Opening/closing mouth | Trigeminal sensory nucleus |
| | | Tensor Tympani muscle | Tension of tympanic membrane | Trigeminal sensory nucleus |
| VI Abducens | Motor | Lateral rectus | Movement of eyeball | Abducens nucleus |
| VII Facial | Sensory | Anterior 2/3 of tongue | Taste | Nucleus Solitarius |
| | Motor | Muscles of facial expression | Facial movement | Facial Motor nucleus |
| | Parasympathetic | Salivary and lacrimal glands via submandibular and pterygopalatine ganglia | Salivation and lacrimation | Superior Salivatory Nucleus |
| VIII Vestibulocochlear | Sensory | Cochlea | Hearing | Cochlear Nucleus |
| | | Vestibular apparatus | Proprioception of head, balance | Vestibular nucleus |

FIG. 6

| Cranial Nerve | Fibers | Structures Innervated | Functions | Brainstem Nucleus |
|---|---|---|---|---|
| IX Glossopharyngeal | Sensory | Eustachian tube, middle ear | General sensation | Trigeminal sensory nucleus |
| | | Carotid Body, and sinus | Chemo/baroreception | Nucleus Solitarius |
| | | Pharynx, posterior 1/3 of tongue | Taste | |
| | Motor | Styropharyngeus | Swallowing | |
| | Parasympathetic | Salivary glands via the otic ganglion | Salivation | Inferior Salivatory nucleus |
| X Vagus | Sensory | Pharynx, larynx, oesophagus, external ear | General sensation | Trigeminal sensory nucleus |
| | | Aortic bodies and arch | Chemo/baroreception | Nucleus Solitarius |
| | | Thoracic and abdominal viscera | Visceral sensation | |
| | Motor | Soft Palate, larynx, pharynx, upper oesophagus | Speech, swallowing | Nucleus Ambiguus |
| | Parasympathetic | Cardiovascular, respiratory, and gastrointestinal systems | Control of these systems | Dorsal Motor nucleus of Vagus |
| XI Accessory | Motor | Sternomastoid, trapezius | Movement of head and shoulders | Nucleus Ambiguus, cranial nerves |
| XII Hypoglossal | Motor | Intrinsic and extrinsic muscles of tongue | Movement of tongue | Hypoglossal nucleus |

FIG. 6 cont'd

METHODS OF TREATING AUTISM USING LIGHT THERAPY

CROSS-REFERENCE TO RELATED APPLICATIONS

This application claims the benefit of U.S. Provisional Application No. 62/435,326 filed Dec. 16, 2016 and is a continuation-in-part of Ser. No. 15/604,363 filed May 24, 2017.

FIELD OF INVENTION

This invention relates generally to methods for treating brain disease. This invention relates more particularly to treating autism non-invasively using light therapy.

BACKGROUND

Neurodegenerative diseases occur when nerve cells in the brain or peripheral nervous system lose function over time and may ultimately die. Neurodegenerative disease is a broad category of brain diseases including autism spectrum disorder; Alzheimer's disease; amyotrophic lateral sclerosis ("ALS"); Creutzfeldt-Jakob disease; vascular dementia; Lewy body dementia; fronto-temporal dementia; multi-infarct dementia; vitamin B-12 deficiency syndrome; hypothyroidism; Huntington's disease; Parkinson's disease; normal pressure hydrocephalus; and tauopathies. Many types of neurodegenerative disease are progressive, in which symptoms gradually worsen over time, and can be fatal. Many of these brain diseases involve inflammation and the body's overall inflammatory response.

Neurodegenerative disease is a common problem in older demographics, causing sufferers to have significant cognitive decline with accompanying increase in cost of care and burden on caregivers. With an ageing population, the problem is likely to worsen. The causes of neurodegenerative diseases are not well known and although there are many studies underway for the treatment of the disease and its symptoms, there is no cure. Current available medications treat the symptoms, but often have unwanted side-effects. It would be desirable to treat patients suffering from neurodegenerative diseases in order to minimize the symptoms, stop the progression of the disease, and ideally to cure it.

Autism spectrum disorder (ASD) is a range of complex neurodevelopment disorders characterized by social impairments, communication difficulties, and restricted, repetitive, and stereotyped patterns of behavior. Autistic disorder, sometimes called autism or classical ASD, is the most severe form of ASD, while other conditions along the spectrum include a milder form known as Asperger syndrome, childhood disintegrative disorder, and pervasive developmental disorder not otherwise specified (PDD-NOS). Evidence suggests that some emotional disorders, such as bipolar disorder, occur more frequently than average in the families of people with ASD.

The cause of ASD is not clearly understood, but it is believed that both genetics and environment likely play a role. A number of genes associated with the disorder have been identified. Studies of people with ASD have found irregularities in several regions of the brain. Other studies suggest people with ASD have abnormal levels of serotonin or other neurotransmitters in the brain, suggesting that ASD could result from the disruption of normal brain development early in fetal development caused by defects in genes that control brain growth and that regulate how brain cells communicate with each other, possibly due to the influence of environmental factors on gene function.

There is no cure and no single best treatment for individuals with autistic disorder. The current standard treatment approach is to customize a customized, highly structured, specialized program or treatment plan incorporating therapies and behavioral interventions targeted toward improving the individual's specific symptoms of autism. Therapies include skill-oriented training sessions to help children develop social and language skills, dietary interventions, and medications to treat anxiety, depression, obsessive-compulsive disorder, or disruptive behaviors associated with autism. The known treatments are complex with often uncertain results, creating a marked challenge for healthcare providers. It would be desirable to treat patients suffering from autism with a relatively simple, non-invasive therapy.

Low-level laser therapy ("LLLT") has been shown through numerous clinical studies and regulatory clearances to be a safe and effective, simple, non-invasive and side-effect free alternative to medication and surgical procedures for the reduction of symptoms in a variety of conditions. LLLT reduces edema, improves wound healing, and relieves pain of various etiologies. It is also used in the treatment and repair of injured muscles and tendons. Application of LLLT has been shown to have the potential to alter cellular metabolism to produce a beneficial clinical effect. Based on its ability to modulate cellular metabolism and alter the transcription factors responsible for gene expression, LLLT has been found to alter gene expression, cellular proliferation, intra-cellular pH balance, mitochondrial membrane potential, generation of transient reactive oxygen species and calcium ion level, proton gradient and consumption of oxygen. LLLT stimulation of the mitochondria via low-energy light has been shown to provoke a dynamic shift in the function of an individual cell. Laser therapy has been shown to stimulate cell regeneration and later gene expression.

It is an object of this invention to apply light energy to a patient's head to treat autism.

SUMMARY OF THE INVENTION

Light energy is applied externally to a patient's head to treat autism. The light is applied to the scalp on the skull near at least the frontal lobes. Optionally the light is also applied to the temporal lobes and the base of the brain. The treatment can be enhanced by activating the cranial nerves while the light is applied.

The wavelengths of the applied light range from about 400-760 nm. In a preferred embodiment the applied light is in the red range and more preferably about of 635 nm±10 nm. The applied light energy is applied with a pulse frequency or frequencies that mimic healthy brain function of alpha, beta, delta, and theta waves such as 8 Hz, 53 Hz, 73 Hz and 101 Hz. The pulse frequencies can be applied singularly, serially, alternately, or simultaneously. The light can be emitted from the same light emitter or from multiple emitters. Preferably the light is laser light and is emitted as a line from a hand-held laser device, and the line is waved manually across a person's skull in the desired area in a continuous, sweeping manner.

DETAILED DESCRIPTION OF THE INVENTION

This invention is a method for treating autism non-invasively by applying light therapy through a patient's scalp and skull to his brain, cranial nerves, or both. There are a number of variables in light therapy, including the wavelength of the light, the power of the light source, the area impinged by the light, the shape of the beam spot when the light impinges the treated area, the pulse frequency, the intensity or fluence of the light energy, and the treatment duration. The setting of these variables typically depends heavily on the disease, brain, skull, and tissue characteristics of the specific patient. The success of each therapy depends on the relationship and combination of these variables. For example, as disclosed in more detail below, Alzheimer's disease may be treated with one regimen utilizing a given power, wavelength, pulse frequency and treatment duration, whereas autism may be treated with a regimen utilizing a different power, wavelength, pulse frequency and treatment duration, and either regimen may be further adjusted for a given patient depending on that patient's size, weight, age, and stage of the disease.

The wavelengths of the light that can be applied range from about 400-760 nm nominal, with the desired wavelength within the spread from nominal. In some embodiments multiple wavelengths are used, either in series, alternately, or simultaneously. The light can be from any source including light-emitting diodes, hard-wired lasers, or laser diodes, but preferably is from a semiconductor laser diode such as Gallium Aluminum Arsenide (GaAlAs) laser diodes, emitting red laser light at 640 nm nominal. Commercial semiconductor laser diodes have a spread of ±10 nm from nominal so the light applied is within the spread from nominal. FIGS. 1, 2, 3 and 5 illustrate probes 14, each containing a laser diode.

The applied light is low-level, typically from emitters of less than 1 W, and preferably from two emitters at 7.5 mW each, for a total of 15 mW. This low-level light therapy has an energy dose rate that causes no immediate detectable temperature rise of the treated tissue and no macroscopically visible changes in tissue structure. Consequently, the scalp tissue impinged by the light, the skull, and the brain and nerve tissue are not heated and are not damaged.

The applied light energy is applied with a pulse frequency or frequencies of brain waves emanating from a healthy brain, as measured by electroencephalography. Brain waves are neural oscillations in a rhythmic or repetitive neural activity that includes the following:

| Wave Type | Approximate Frequency Range in Humans | Main Source Location on the Human Brain |
|---|---|---|
| Delta | 0.5 to 3 Hz 0.5-4 | thalamus or cortex |
| Theta | 3 to 8 Hz | hippocampus |
| Alpha | 8-12.5 Hz | occipital lobe |
| Mu | 7.5-12.5 (and primarily 9-11) Hz | motor cortex |
| Beta | 12.5 to 38 Hz | posterior brain |
| Gamma | 38 to 100 Hz | all areas of brain |

Other types of oscillatory activity are found in a healthy central nervous system, and light therapy may be applied at a pulse frequency that mimics that oscillatory activity. Multiple pulse frequencies can be applied singularly, serially, alternately, or simultaneously. In one embodiment, the light therapy is applied using several light sources, each having a different frequency.

Light is applied to the patient's head 11. The light may be applied to a patient's shaved skull 11a, through the patient's hair, or through a translucent skull cap 20 which may also aid in orienting the light to the desired location on the patient's head. Typically the patient is treated while the patient is vertical or nearly vertical, as opposed to prone or supine, so that all regions of the skull and brain stem can be treated without moving the patient. Usually the patient is seated in a chair. The patient can be awake, sedated, or asleep.

Figure 4:
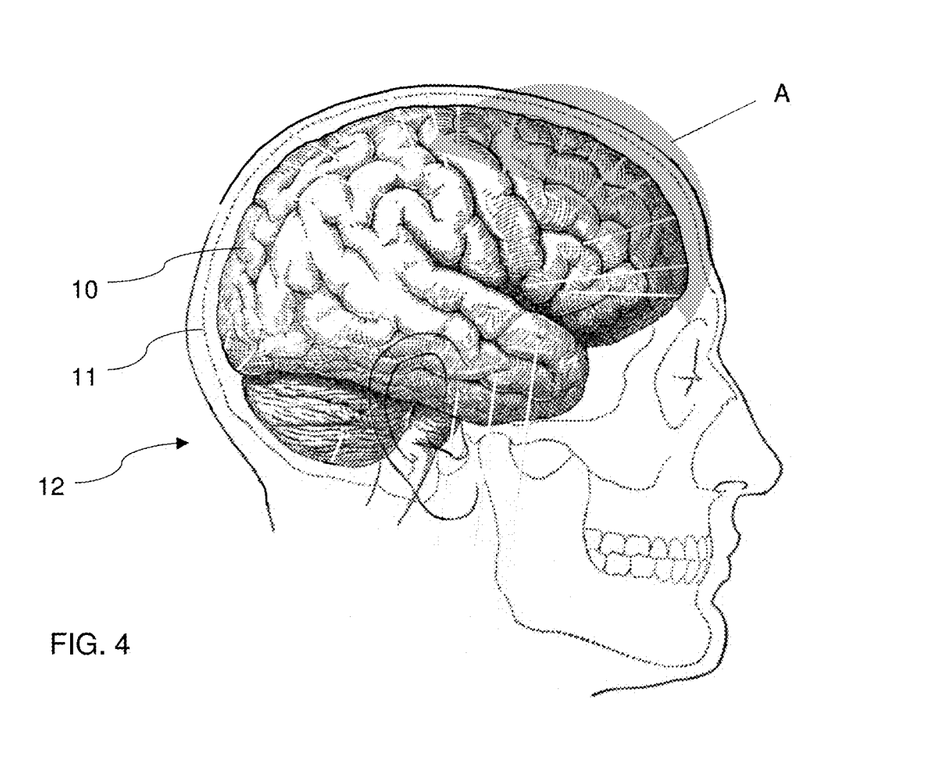
FIG. 4 is a schematic illustration of a brain inside a patient's skull.
Figure 5:
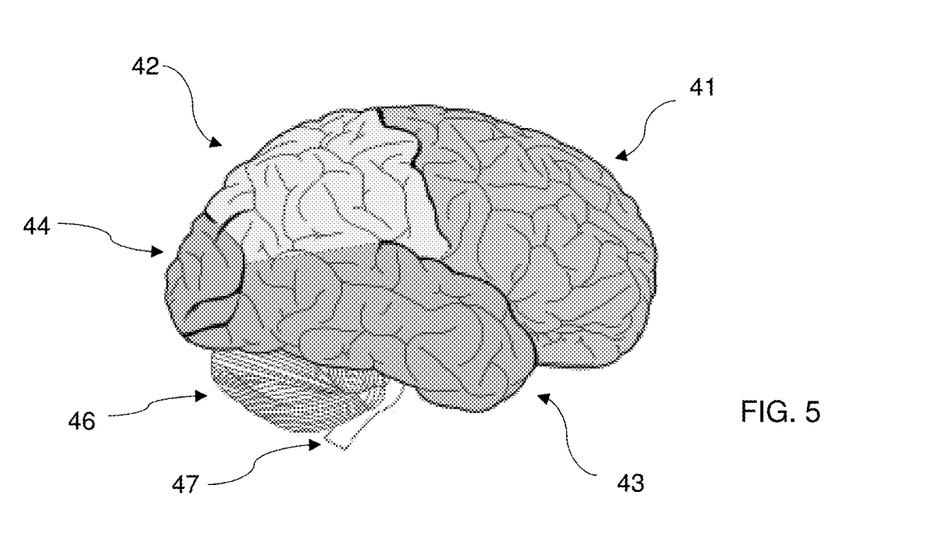
FIG. 5 is a schematic illustration of a brain.
Figure 6:
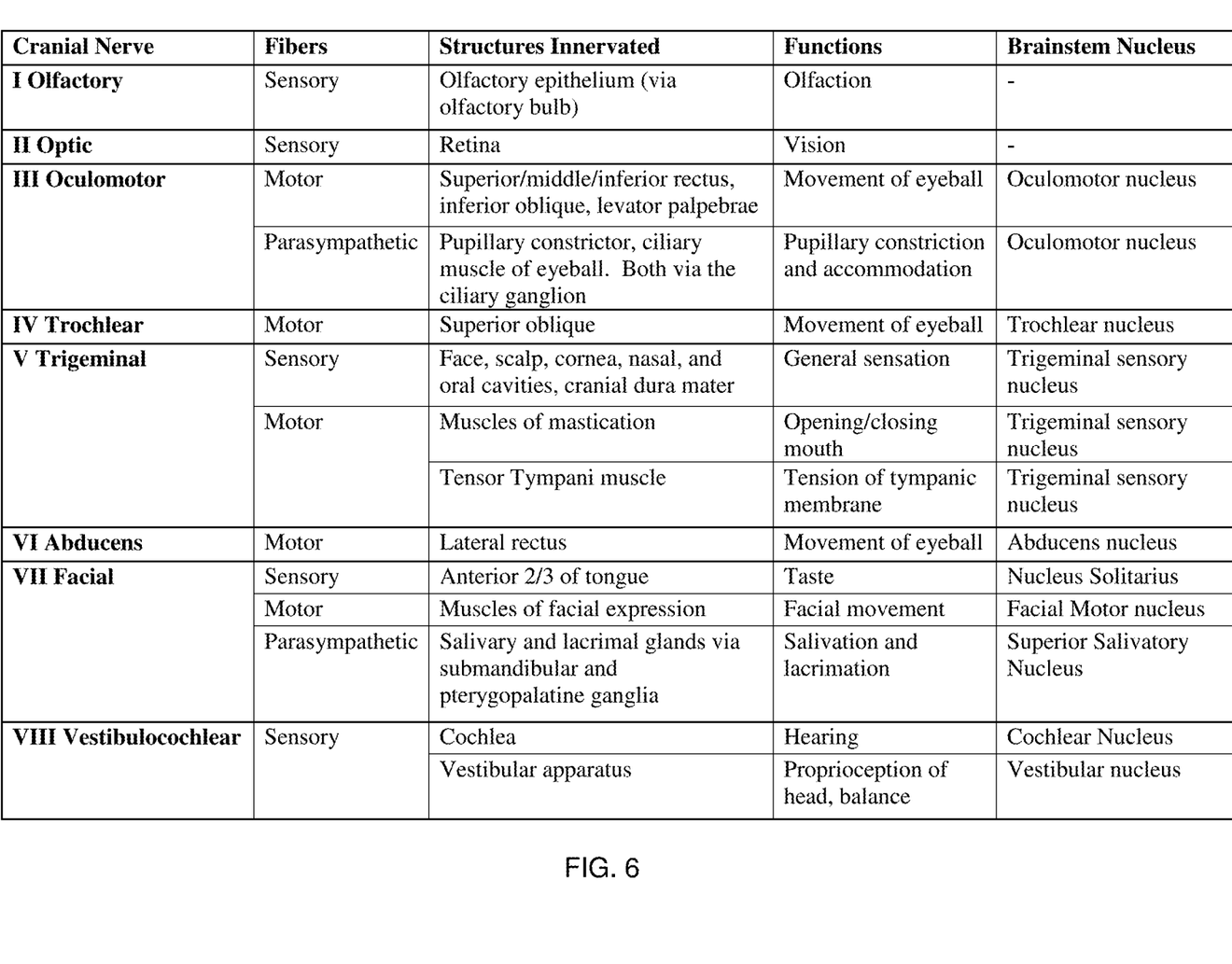
FIG. 6 is a prior-art table of cranial nerves.

The method is non-invasive. The light is applied to the skull near the area of the brain or cranial nerves (or both) that is malfunctioning or associated with the source of the malady to be treated, if the area is known. As used herein, light applied "near the" area means light applied to the scalp at a position mapped to the area of the brain to be treated, such as the frontal 41, parietal 42, temporal 43, and occipital 44 lobes; the cortex; cerebellum; the brain stem or base of the brain; or where one or more cranial nerves enters the brain. See FIG. 5. For example, if the light is to be applied "near the frontal lobes," it will be applied to the scalp above the frontal cortex, as indicated generally by area A in FIG. 4. In another example, if the light is to be applied "near the area" of the basal ganglia, which is in the center of the brain, the light will be applied to the scalp all around the head from about the ear lobes up to the top of the head. The treatment can be enhanced by activating the cranial nerves while the light is applied. FIG. 6. Is a table of the cranial nerves and their functions. A cranial nerve is activated by having the patient to execute the function indicated the table of FIG. 6. For example, to activate the olfactory nerve, the patient would be given something with an odor or scent to smell. Similarly, to activate the trochlear nerve, the patient would move his eyeballs.

The following table sets forth some of the locations to be treated for specific diseases:

| Disease | Main location to be treated on the human brain |
|---|---|
| Alzheimer's | frontal cortex, temporal lobe and base of brain |
| Amyotrophic lateral sclerosis ("ALS") | motor cortex |
| Autism spectrum disorder | frontal lobes, temporal lobe and base of brain |
| Epileptic seizures | cortex |
| Huntington's disease | basal ganglia |
| Parkinson's disease | midbrain |
| Pick's disease and other fronto-temporal dementias | frontal lobe |

Some diseases are not area-specific. That is, some diseases are not necessarily due to a specific damaged area of the brain, instead occurring throughout the brain, or at a different location for each patient, such as Creutzfeldt-Jakob disease, hypothyroidism, Lewy body dementia, normal pressure hydrocephalus, tauopathies, and vascular dementia. For example, with vascular dementia, blood vessels through the brain may be affected, some more than others. For these maladies the light is applied all over the head. For an inflammation-based disease such as Parkinson's, the more areas of the brain that can be treated the more effective treatment is. In fact, due to the systemic effects of applying light anywhere to the brain, the application of light on any area of the skull will work on any malady to some degree, and application to multiple areas is often beneficial. In one embodiment the treatment is applied to a specific hemisphere of the brain. For some diseases the treatment is applied to acupuncture points on the brain.

Figure 1:
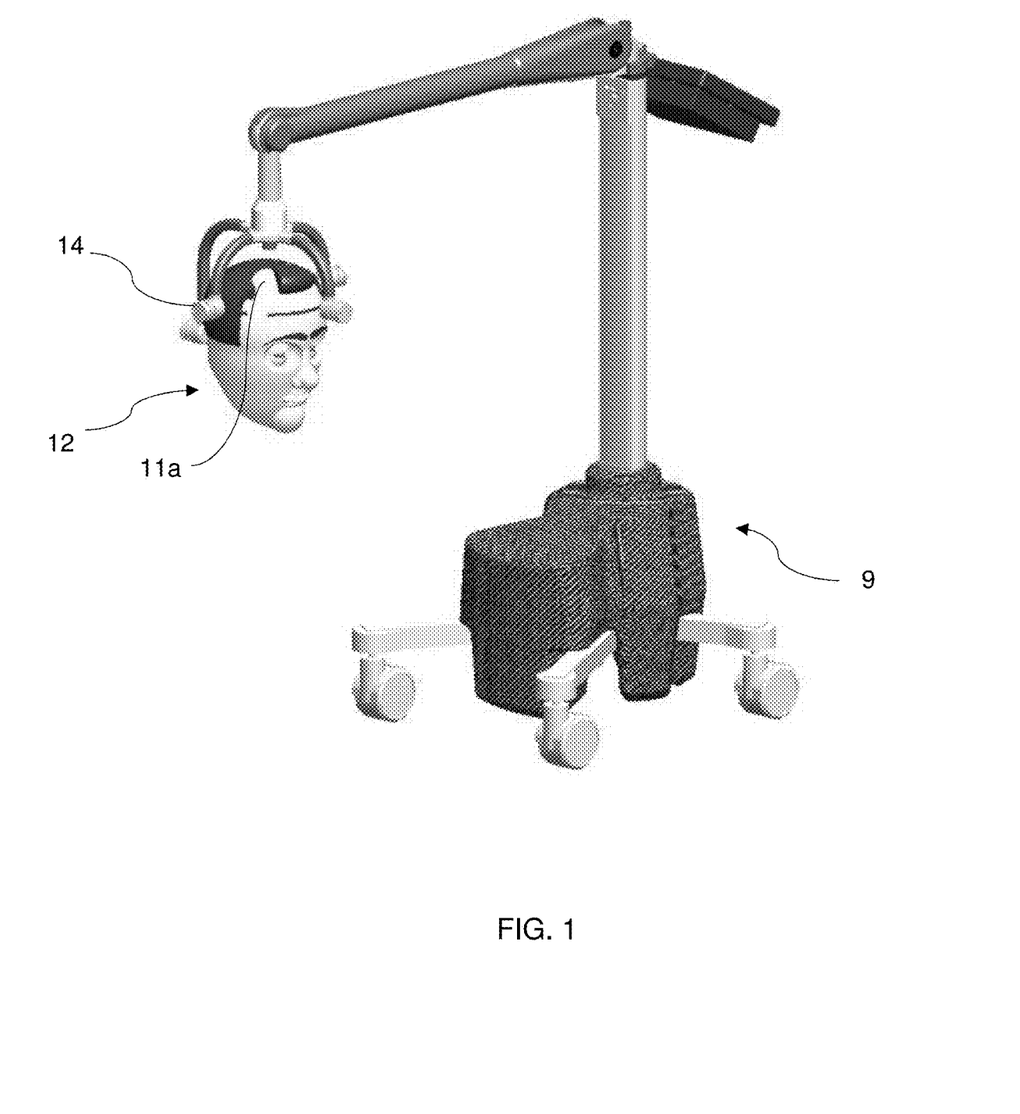
FIG. 1 illustrates a portable, floor-supported light-emitting device for treating a patient's head.

Another variable in the light treatment parameters is the intensity or fluence of the light energy. Bio stimulation occurs with the application of between 0.001 to 5 joules of energy. For example, U.S. Pat. No. 7,118,588, incorporated here by reference, discloses a line generator for laser light application. At 4 inches away from the scalp, the 70 degree line generator as disclosed therein creates a projected beam that is 14 cm long and 3 mm wide for a total beam area of 420 $mm^2$. The size of each treatment area is the same as the beam profile because the diode is not moved during procedure administration. Given a 600 second treatment time with a 7.5 mW laser, the total energy each produced by each independent laser diode is 4.5 joules per laser. The fluence per laser is calculated as 0.011 $J/cm^2$. Using a laser with 5 independent laser diodes, as shown in FIG. 1, each laser diode treats a different (separate) areas of the head, so the fluence remains the same (unchanged) at 0.011 joules; however, the total energy delivered to the subject per 10-minute procedure administration across all 5 laser diodes and respective treatment areas combined is 22.5 joules.

Figure 2:
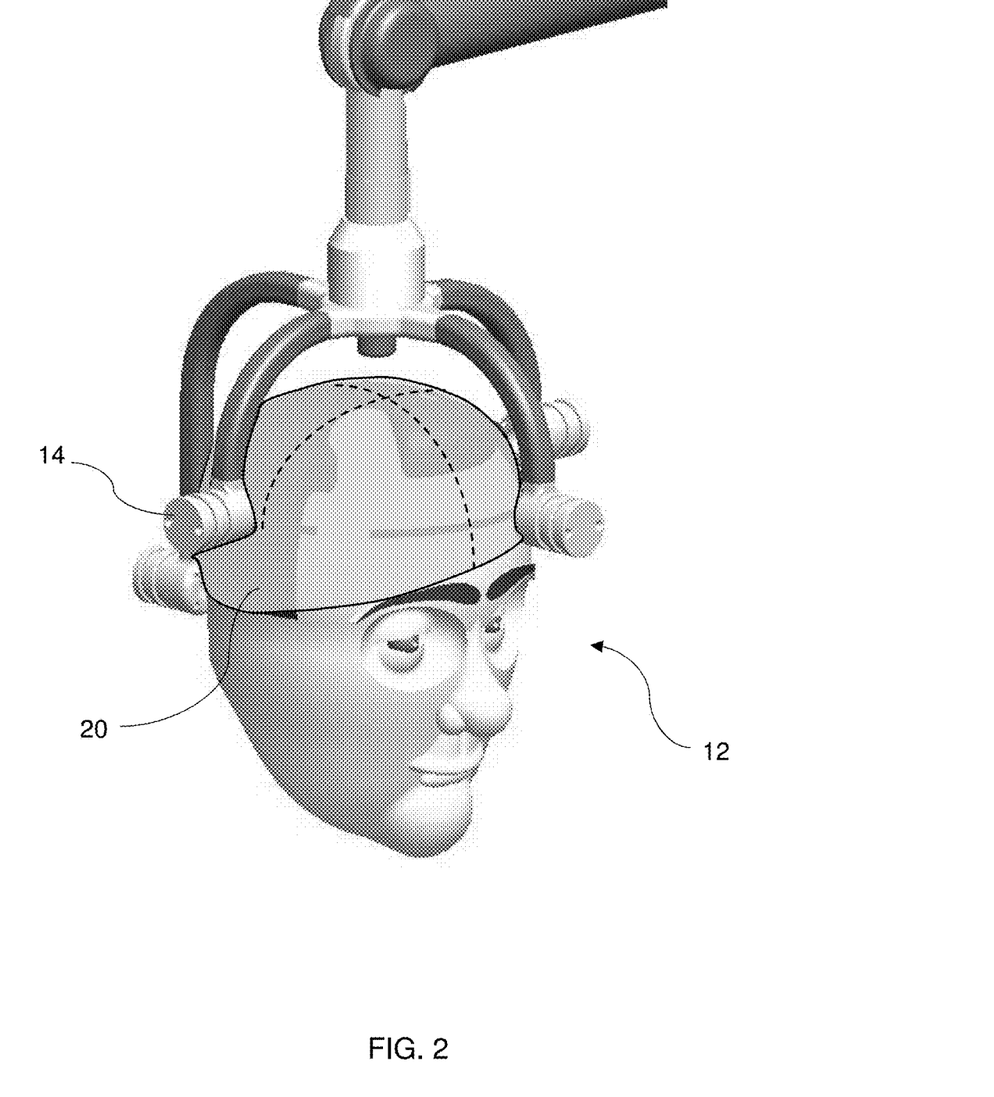
FIG. 2 illustrates the light-emitting device of FIG. 1 employing a translucent cap around a patient's head.
Figure 3:
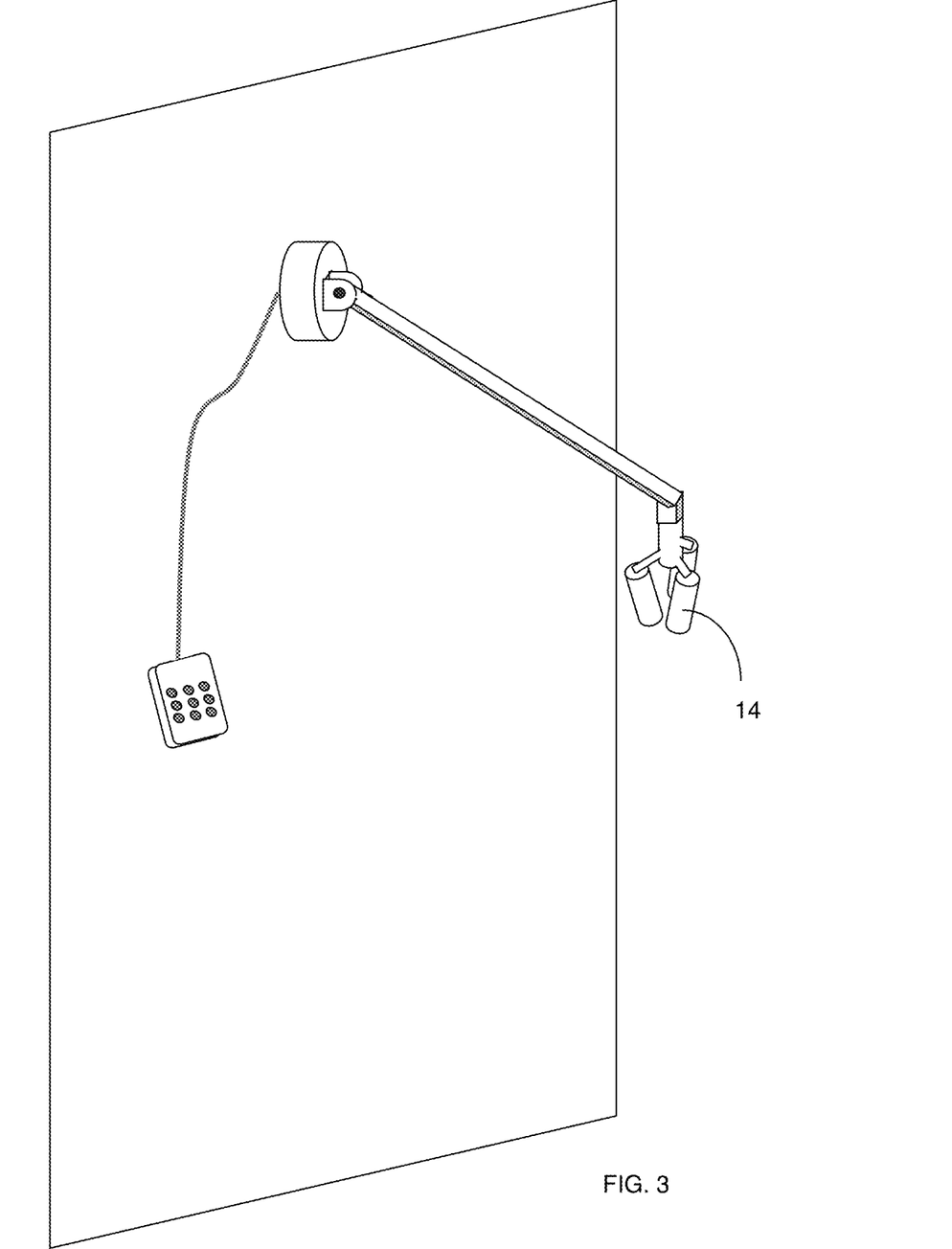
FIG. 3 illustrates a wall mounted light-emitting device for treating a patient's head.

The laser energy can be applied to the patient using a variety of laser devices, such as a hand-held laser device, a full-body laser scanner, a wall-mounted laser device, or a stand-alone laser device. Handheld lasers are described in U.S. Pat. Nos. 6,013,096 and 6,746,473, which are incorporated herein by reference. A full-body laser scanner is described in U.S. Pat. No. 8,439,959, incorporated herein by reference. Wall-mount and stand-alone lasers 9 are described in U.S. Pat. No. 7,947,067 as illustrated in FIGS. 1 and 2 and incorporated herein by reference.

In a preferred embodiment, the light is emitted in a line and the line is waved manually across a person's skull in the desired area in a continuous, sweeping manner. In another embodiment the shape of the beam spot on the treated area is an apparent circle, which is actually a rotating diameter by a line of light. U.S. Pat. No. 7,922,751, incorporated herein by reference, discloses a device to sweep such a circular beam spot. The device disclosed in that patent can be programmed to move the scanning head in a manner to achieve any desired shape of a treatment zone on the head of a patient. A sample selection of available scan patterns is shown in that patent at FIGS. 8a-h.

Alzheimer's Example

In one example light therapy is applied to patients with mild to moderate Alzheimer's disease improve their memory, thinking and behaviors. The light-emitting device is a mains powered variable hertz laser device made up of five independent red laser diodes mounted in scanner devices and positioned equidistant from each other. Each scanner emits 7.5 milliwatts (m)±1.0 mW 640 nanometers (nm) with a tolerance of ±10 nm of red laser light.

The laser energy is administered to each patient's frontal cortex, temporal regions and base of the skull 8 times across 4 consecutive weeks, 2 times each week, for 10 minutes of treatment time during each of 8 treatments. The total energy delivered to the patient per procedure administration is 22.5 joules. The patient's frontal cortex, temporal regions and the base of the skull are lazed equally in a continuous sweeping motion continuously during the 10-minute treatment session using pulse frequencies of 8 Hz, 53 Hz, 73 Hz and 101 Hz. The laser energy is applied four inches from the skin surface, and the laser light is directed perpendicular to the plane of the skin ensuring that the beam is penetrating perpendicular to the skin.

The treatment for patients with autism preferably utilizes red laser energy at 635 nm±10 nm, from one or more 7.5 mW±1.0 mW semiconductor laser diodes. Each treatment uses one or more pulse frequencies at 8 Hz, 53 Hz, 73 Hz and 101 Hz. The length of each treatment is 2-12 minutes, and preferably 5 or 10 minutes. The number of treatments varies, depending on that patient's size, weight, age, and severity of the autism symptoms. Patients may see improvement after a single treatment, but typically see improvement after 6 treatments. Treatments may be given periodically or as needed after the initial set of treatments to maintain or further improve the symptoms.

Autism Example #1

Children exhibiting autistic behaviors are treated with low-level laser by scanning each patient's frontal cortex, temporal area and the base of the brain for 10 minutes, twice weekly, 3-4 days apart, for three consecutive weeks, for a total of 6 treatments. The patient's frontal cortex, temporal area and the base of the brain are lazed equally in a continuous sweeping motion continuously during the 10-minute treatment session using pulse frequencies of 8 Hz, 53 Hz, 73 Hz and 101 Hz. The light-emitting device used comprised a hand-held laser device with two 7 mW red semiconductor laser diodes emitting a line of red laser light at a wavelength of 635 nm±5 nm. Changes in behavior are measured using the Aberrant Behavior Checklist ("ABC"). Significant improvements are achieved in all 5 ABC Subscales and the ABC global score. No adverse events occurred.

Autism Example #2

Children exhibiting autistic behaviors are treated with low-level laser by scanning each patient's temporal areas and the base of the brain for 5 minutes, twice weekly, 3-4 days apart, for four consecutive weeks, for a total of 8 treatments. The patient's temporal regions and the base of the brain are lazed equally in a continuous sweeping motion continuously during the 5-minute treatment session using pulse frequencies of 8 Hz, 53 Hz, 73 Hz and 101 Hz. The light-emitting device used comprises a hand-held laser device with two 7 mW red semiconductor laser diodes emitting a line of red laser light at a wavelength of 635 nm±5 nm.

Autism Example #3

A patient suffering from autism symptoms is treated with a 15 mW hand-held laser device, emitting a line of red laser light at a wavelength of 635 nm±5 nm from semiconductor laser diodes. The line of laser light is manually scanned on the front of the patient's head near the frontal lobes using one or more pulse frequencies of 8 Hz, 53 Hz, 73 Hz and 101 Hz. The patient is treated for 5 minutes in each treatment, having two treatments per week for four weeks.

Autism Example #4

A patient suffering from autism symptoms is treated with a 15 mW hand-held laser device, emitting a line of red laser light at a wavelength of 635 nm±5 nm from semiconductor laser diodes. The line of laser light is manually scanned on the front of the patient's head near the frontal lobes and on the patient's head near the temporal lobes. The patient is treated for 5 minutes in each treatment, twice weekly, 3-4 days apart, for four consecutive weeks, for a total of 8 treatments.

Autism Example #5

A patient suffering from autism symptoms is treated with hand-held laser device that has two 7.5 mW semiconductor laser diodes, emitting lines of red laser light at a wavelength of 635 nm±5 nm. The laser light is manually scanned on the front of the patient's head near the frontal lobes, on the patient's head near the temporal lobes, and on the patient's head near the base of the brain. The patient is treated for 5 minutes in each treatment, having treatments 3-4 times per week for four weeks.

While there has been illustrated and described what is at present considered to be the preferred embodiments of the present invention, it will be understood by those skilled in the art that various changes and modifications may be made and equivalents may be substituted for elements thereof without departing from the true scope of the invention. Therefore, it is intended that this invention not be limited to the particular embodiments disclosed, but that the invention will include all embodiments falling within the scope of the appended claims.

The invention claimed is:

1. A method of treating autism in a patient comprising applying low-level laser energy directly to two or more locations on the patient's head in a continuous sweeping manner motion, using a hand-held laser device that emits a line of laser light wherein the laser energy is applied to at least one location on the patient's head that is above the glabellomeatal and infraorbitomeatal lines, wherein the direct application of laser energy causes no detectable temperature rise of the treated location, wherein the laser energy has a wavelength above 400 nm and below infrared wavelengths, and wherein the laser energy is applied directly to at least one location on the patient's head near the frontal lobes of the patient's brain.

2. The method of claim 1 wherein the laser energy has a wavelength in the red range.

3. The method of claim 1 wherein the laser energy has a wavelength of 635 nm±10 nm.

4. A method of treating autism in a patient comprising applying low-level laser energy in a continuous sweeping motion directly to two or more locations on the patient's head for one or more treatments, wherein laser energy is applied to at least one location on the patient's head above the glabellomeatal and infraorbitomeatal lines, wherein each treatment is 2-10 minutes long, wherein the direct application of laser energy causes no detectable temperature rise of the treated location, wherein the laser energy has a wavelength above 400 nm and below infrared wavelengths and wherein the laser energy is applied directly to at least one location on the patient's head near the frontal lobes of the patient's brain.

5. The method of claim 4 wherein the laser energy has a wavelength of 635 nm±10 nm.

6. The method of claim 4 wherein each treatment applies 0.001—5.0 joules of energy to the patient's head.

7. The method of claim 1 wherein the laser energy is emitted from laser energy sources of 7.5 mW or less.

8. The method of claim 1 wherein the laser energy has a power density of 1.78 mW/cm2.

9. The method of claim 4 wherein the laser energy is emitted from laser energy sources of 7.5 mW or less.

10. The method of claim 4 wherein the laser energy has a power density of 1.78 mW/cm2.

11. A method of treating autism in a patient comprising applying low-level laser energy to two or more locations on the patient's head in a continuous sweeping manner motion, using a hand-held laser device that emits a line of laser light wherein the laser energy is applied to at least one location on the patient's head that is above the glabellomeatal and infraorbitomeatal lines, wherein:
   a. the application of laser energy is free from intervening temperature-reducing elements between the laser device and the patient's head and causes no detectable temperature rise of the treated location; and
   b. the laser energy has a wavelength above 400 nm and below infrared wavelengths and wherein the laser energy is applied directly to at least one location on the patient's head near the frontal lobes of the patient's brain.

12. The method of claim 11 wherein the laser energy has a wavelength in the red range.

13. The method of claim 11 wherein the laser energy has a wavelength of 635 nm±10 nm.

14. The method of claim 11 wherein the laser energy is emitted from laser energy sources of 7.5 mW or less.

15. The method of claim 11 wherein the laser energy has a power density of 1.78 mW/cm2.

16. The method of claim 11 wherein the laser energy is applied for one or more treatments, wherein each treatment is 2-12 minutes long.

* * * * *